United States Patent [19]

Hurter

[11] Patent Number: 4,602,084
[45] Date of Patent: Jul. 22, 1986

[54] MONOAZO DYES CONTAINING A 4-SUBSTITUTED-2-AZO-1,1'-DIPHENYL-SULFONE COMPONENT

[75] Inventor: Rudolf Hurter, Basel, Switzerland

[73] Assignee: Ciba-Geigy Corporation, Ardsley, N.Y.

[21] Appl. No.: 512,089

[22] Filed: Jul. 8, 1983

[30] Foreign Application Priority Data

Jul. 19, 1982 [CH] Switzerland .................. 4397/82

[51] Int. Cl.⁴ .................. C09B 29/01; C09B 29/033; C09B 29/036; C09B 62/006
[52] U.S. Cl. .................. 534/641; 260/456 A; 534/630; 534/631; 534/638; 534/640; 534/642; 534/643; 534/644; 534/730; 534/731; 534/739; 534/749; 534/750; 534/752; 534/753; 534/770; 534/771; 534/772; 534/780; 534/782; 534/783; 534/790; 534/793; 534/844; 534/845; 534/847; 534/848; 534/860; 534/861; 534/882; 260/507 R; 260/509; 260/510
[58] Field of Search ........... 260/205, 206, 207, 207.1, 260/152, 157, 158, 165, 163, 162, 196, 197, 198, 199, 200, 201; 534/862, 860, 845, 780, 750, 749, 739, 640, 643, 631, 630, 638, 641, 642, 644, 752, 753, 787, 790, 730, 731, 770, 771, 772, 782, 783, 844, 847, 848, 861, 882

[56] References Cited

U.S. PATENT DOCUMENTS

| | | |
|---|---|---|
| 2,449,130 | 9/1948 | Krebser et al. .................. 260/199 |
| 2,551,887 | 5/1951 | Kuster .................. 260/199 |
| 3,417,076 | 12/1968 | Sartori .................. 260/205 |
| 3,692,769 | 9/1972 | Weaver et al. .................. 260/207.1 |
| 3,951,944 | 4/1976 | Fuchs .................. 260/186 |
| 4,042,580 | 8/1977 | Groebke .................. 260/207 |
| 4,046,757 | 9/1977 | Meybeck et al. .................. 260/207 |
| 4,052,444 | 10/1977 | Laubert et al. .................. 260/507 |
| 4,119,624 | 10/1978 | Boyd et al. .................. 260/207.1 |
| 4,193,916 | 3/1980 | Back et al. .................. 260/146 R |
| 4,267,104 | 5/1981 | Giles et al. .................. 260/207.3 |

FOREIGN PATENT DOCUMENTS

| | | | |
|---|---|---|---|
| 0039306 | 3/1981 | European Pat. Off. .................. 260/205 |
| 0042357 | 6/1981 | European Pat. Off. .................. 260/165 |
| 2021615 | 12/1979 | United Kingdom .................. 260/154 |

Primary Examiner—Floyd D. Higel
Attorney, Agent, or Firm—Wenderoth, Lind & Ponack

[57] ABSTRACT

Monoazo dyes of the formula

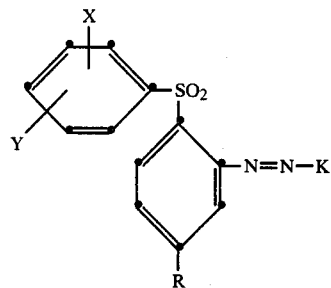

(1)

in which K is the radical of a coupling component of the benzene or naphthalene series or of the heterocyclic series, and R is a

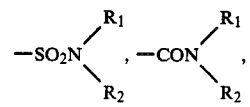

$-CO-R_2$ or $-SO_2-O-R_2$ group in which $R_1$ is hydrogen or $C_{1-4}$-alkyl and $R_2$ is a substituted or unsubstituted monosulfo-$C_{1-12}$-alkyl radical, a substituted or unsubstituted monosulfophenyl, disulfophenyl, monosulfonaphthyl or disulfonaphthyl radical, and X and Y, independently of each other, are hydrogen, $C_{1-4}$-alkyl, $C_{1-4}$-alkoxy, halogen, $C_{2-6}$-alkanoylamino, $C_{1-5}$-alkylsulfonylamino or a substituted or unsubstituted phenyl or phenoxy radical, produce dyeings on polyamide material which have good light and wet fastness properties.

7 Claims, No Drawings

MONOAZO DYES CONTAINING A 4-SUBSTITUTED-2-AZO-1,1'-DIPHENYLSULFONE COMPONENT

The object of the present invention is to provide novel monoazo dyes which are suitable for dyeing natural and synthetic polyamides from an aqueous bath, which have hues within the yellow to red region, and which also have improved fastness properties, in particular an improved light fastness.

We have found, then, that the monoazo dyes of the formula (1) achieve this object.

The invention thus relates to monoazo dyes of the formula

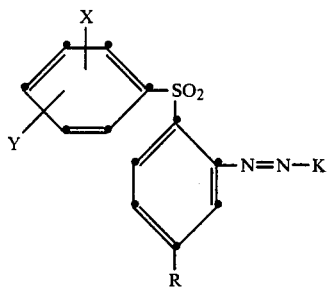

(1)

in which K is the radical of a coupling component of the benzene or naphthalene series or of the heterocyclic series, R is a

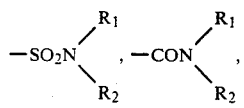

—CO—$R_2$ or —$SO_2$—O—$R_2$ group in which $R_1$ is hydrogen or $C_{1-4}$-alkyl and $R_2$ is a substituted or unsubstituted monosulfo-$C_{1-12}$-alkyl radical, a substituted or unsubstituted monosulfophenyl, disulfophenyl, monosulfonaphthyl or disulfonaphthyl radical, and X and Y, independently of each other, are hydrogen, $C_{1-4}$-alkyl, $C_{1-4}$-alkoxy, halogen, $C_{2-6}$-alkanoylamino, $C_{1-5}$-alkylsulfonylamino or a substituted or unsubstituted phenyl or phenoxy radical.

The radical K of a coupling component can contain the substituents customary in the case of azo dyes, for example alkyl groups having 1 to 4 carbon atoms, such as methyl, ethyl, propyl, isopropyl, butyl, isobutyl, sec.-butyl and tert.-butyl, alkoxy groups having 1 to 4 carbon atoms, such as methoxy, ethoxy, propyloxy, isopropyloxy, butyloxy, isobutyloxy, sec.-butyloxy and tert.-butyloxy, phenoxy, alkanoylamino groups having 1 to 6 carbon atoms, such as acetylamino or propionylamino, benzoylamino, amino groups, such as —$NH_2$, methylamino, ethylamino, dimethylamino, diethylamino, cyanoethylamino, hydroxyethylamino, dihydroxyethylamino, cyclohexylamino, benzylamino and phenylamino, carboxylic acid ester groups, such as methoxycarbonyl and ethoxycarbonyl, trifluoromethyl, nitro, cyano, acetyl, methylsulfonyl, carbamoyl, sulfamoyl, ureido, hydroxyl, carboxyl, sulfo, sulfomethyl and halogen, such as fluorine, chlorine and bromine, as well as fibre-reactive radicals.

K is preferably the radical of an aminobenzene, alkoxybenzene, aminonaphthalene, alkoxynaphthalene, naphthol, aminonaphthol, pyrazolone, aminopyrazole, pyridone, pyrimidine, indole, naphthylimidazole, diphenylamine, pyrazolo[2,3-a]pyrimidine, tetrahydroquinoline or acetoacetamide, which radicals can be further substituted.

$C_{1-4}$-alkyl radicals $R_1$, X or Y in the formula (1) are independently of one another for example methyl, ethyl, propyl, isopropyl, butyl, sec.-butyl, isobutyl or tert.-butyl radicals.

A monosulfo-$C_{1-12}$-alkyl radical $R_2$ is for example a straight-chain or branched monosulfoalkyl radical, which can be further substituted, for example by halogen, such as fluorine, chlorine or bromine, hydroxyl, cyano, $C_{1-4}$-alkoxy, such as methoxy, ethoxy, propoxy, isopropoxy, butoxy, sec.-butoxy, tert.-butoxy or isobutoxy, and alkanoyl groups having 1 to 6 carbon atoms, such as the acetyl or propionyl group, and the benzoyl group. Examples of $R_2$ for use as a monosulfo-$C_{1-12}$-alkyl radical are sulfomethyl, β-sulfoethyl, γ-sulfopropyl and δ-sulfobutyl. A monosulfoalkyl radical $R_2$ is preferably a β-sulfoethyl radical.

A substituted or unsubstituted monosulfophenyl or disulfophenyl radical $R_2$ is preferably a radical of the formula

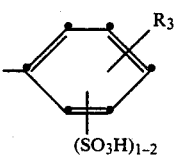

(2)

in which $R_3$ is hydrogen, $C_{1-4}$-alkyl, for example methyl, ethyl, propyl, isopropyl, butyl, isobutyl, sec.-butyl and tert.-butyl, $C_{1-4}$-alkoxy, for example methoxy, ethoxy, propoxy, isopropoxy, butoxy, isobutoxy, sec.-butoxy and tert.-butoxy, halogen, for example fluorine, chlorine and bromine, $C_{2-6}$-alkanoylamino, for example acetylamino, propionylamino and butyrylamino, or carboxyl. The following are mentioned by way of example: the 2-, 3- or 4-sulfophenyl, 2,5-disulfophenyl, 4-acetylamino-3-sulfophenyl, 2-chloro-5-sulfophenyl, 2-carboxy-4-sulfophenyl, 2-methyl-4-sulfophenyl, 2-methoxy-5-sulfophenyl, 4-methyl-3-sulfophenyl and 4-chloro-3-sulfophenyl radical.

A substituted or unsubstituted monosulfonaphthyl or disulfonaphthyl radical $R_2$ is preferably a radical of the formula

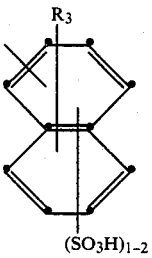

(3)

in which $R_3$ is as defined under the formula (2). The following are mentioned by way of example: the 1-sulfonaphth-2-yl, 6-sulfonaphth-2-yl and 1,5-disulfonaphth-2-yl radicals.

$C_{1-4}$-alkoxy radicals X and Y are independently of each other for example methoxy, ethoxy, propoxy, isopropoxy, butoxy, isobutoxy, sec.-butoxy or tert.-butoxy radicals.

Halogens X and Y are independently of each other for example fluorine, chlorine or bromine atoms.

$C_{2-6}$-alkanoylamino radicals X and Y are independently of each other for example acetylamino or propionylamino radicals.

Phenyl radicals X and Y can be further substituted, for example by $C_{1-4}$-alkyl groups, such as methyl, $C_{1-4}$-alkoxy groups, such as methoxy and ethoxy, halogen, such as fluorine, chlorine or bromine, alkanoylamino groups having 1 to 6 carbon atoms, such as acetylamino, hydroxyl and carboxyl.

Phenoxy radicals X and X are independently of each other preferably phenoxy radicals which can be further substituted in the phenyl moiety as indicated above.

In preferred monoazo dyes of the formula (1), Y is hydrogen, chlorine or methoxy.

In preferred monoazo dyes of the formula (1), X is bonded to the phenyl ring in p-position relative to the —$SO_2$ group.

Monoazo dyes of the formula (1) can be substituted in the coupling component K by fibre-reactive groups.

Examples of suitable fibre-reactive groups are those of the aliphatic series, such as acryloyl, mono-, di- or trichloroacryloyl, mono-, di- or tribromoacryloyl, mono-, di- or trichlorometacryloyl, or mono-, di- or tribromometacryloyl, such as —CO—CH=CH—Cl, —CO—CCl=$CH_2$, —CO—CH=CHBr, —COCBr=$CH_2$, —CO—CBr=CHBr, —CO—CCl=CH—$CH_3$, and also —CO—CCl=CH—COOH, —CO—=CCl—COOH, 3-chloropropionyl, 3-phenylsulfonylpropionyl, 3-methylsulfonylpropionyl, β-sulfatoethylaminosulfonyl, vinylsulfonyl, β-chloroethylsulfonyl, β-sulfatoethylsulfonyl, β-methylsulfonylethylsulfonyl, β-phenylsulfonylethylsulfonyl, 2-fluoro-2-chloro-3,3-difluorocyclobutane-1-carbonyl, 2,2,3,3-tetrafluorocyclobutanecarbon-1-yl, 2,2,3,3-tetrafluorocyclobutane-sulfon-1-yl, β-(2,2,3,3-tetrafluorocyclobut-1-yl)acryloyl, α- or β-alkylsulfonylacryloyl or -arylsulfonylacryloyl, such as α- or β-methylsulfonylacryloyl.

Reactive radicals which are particularly suitable for synthetic polyamide and for wool are chloroacetyl, bromoacetyl, α,β-dichloropropionyl, α,β-dibromopropionyl, α- chloroacryloyl or β-bromoacryloyl, 2,4-difluoro-5-chloropyrimid-6-yl, 2,4,6-trifluoropyrimid-5-yl, 2,4-dichloro-5-methylsulfonylpyrimidin-6-yl, 2,4-difluoro-5-methylsulfonylpyrimid-6-yl, 2,4-difluorotriazin-6-yl, and fluorotriazinyl radicals of the formula

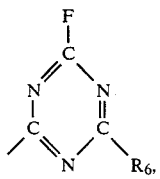

in which $R_6$ is a substituted or unsubstituted amino group or a free or etherified oxy or thio group, for example the $NH_2$ group, a $C_1$-$C_4$-alkyl-monosubstituted or -disubstituted amino group, a $C_1$-$C_4$-alkoxy group, a $C_1$-$C_4$-alkylmercapto group, arylamino, in particular phenylamino, or methyl-, methoxy-, chlorine- and, especially, sulfo-substituted phenylamino, phenoxy, mono- or disulfophenoxy and the like, and the corresponding chlorotriazinyl radicals.

Examples of starting materials for introducing such triazine radicals are 2,4-difluoro- or 2,4-dichloro-6-aminotriazine, 2,4-difluoro- or 2,4-dichloro-6-methylaminotriazine, 2,4-difluoro- or 2,4-dichloro-6-ethylaminotriazine, 2,4-difluoro- or 2,4-dichloro-6-phenylaminotriazine, 2,4-difluoro- or 2,4-dichloro-6-(2',3'- or 4'-sulfophenyl)-aminotriazine, 2,4-difluoro- or 2,4-dichloro-6-(2',4' or 3',4'- or 2',5'- or 4',5'-disulfophenyl)-aminotriazine, 2,4-difluoro- or 2,4-dichloro-6-dimethylaminotriazine, 2,4-difluoro or 2,4-dichloro-6-methoxytriazine, 2,4-difluoro- or 2,4-dichloro-6-(β-methoxyethoxy)-triazine, 2,4-difluoro- or 2,4-dichloro-6-methylmercaptotriazine and 2,4-difluoro or 2,4-dichloro-6-phenylmercaptotriazine and 2,4,6-trifluoro or 2,4,6-trichlorotriazine.

In preferred monoazo dyes of the formula (1), K is an N-$C_{1-4}$-alkylaminobenzene or N,N-di-$C_{1-4}$-alkylaminobenzene radical which can be substituted in the benzene ring by methyl, chlorine, acetylamino and benzoylamino and in which the N-alkyl radicals can be substituted independently of each other by hydroxyl, chlorine, cyano, phenyl or sulfophenyl, a methoxybenzene radical, a methoxynaphthalene radical, an aminonaphthalene radical which can be substituted by sulfo, a hydroxynaphthalene radical which can be substituted by sulfo, an aminonaphthol radical which can be substituted in the naphthalene nucleus by sulfo and in which the amino group can be substituted by methyl, α,β-dibromopropionyl, α,β-dibromopropionylaminobenzoyl and 2,6-difluoro-5-chloropyrimidylaminobenzoyl, a 1-phenyl-3-methylpyrazolone radical which can be substituted in the phenyl radical by chlorine and methyl, a 1-phenyl-3-methylaminopyrazole radical which can be substituted in the phenyl radical by chlorine and sulfo, a 1-ethyl-4-methyl-6-hydroxypyrid-2-one radical which can be substituted in the 3-position by carbamoyl, a 2,4,6-triaminopyrimidine radical, a 2-methylindole or 1-ethyl-2-methylindole radical, a 1-chlorophenylamino-2-methylnaphthimidazole radical or 2-pentylnaphthimidazole radical, substituted in the naphthalene nucleus by hydroxyl and sulfo, an N-methyl or N-ethyl-1,2,3,4-tetrahydroquinoline radical, or a 2,5-dimethyl-7-aminopyrazolo[2,3-a]pyrimidine radical, and R is a

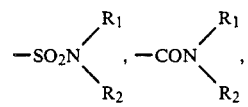

—CO—$R_2$ or —$SO_2$—O—$R_2$ group in which $R_1$ is hydrogen or methyl, and $R_2$ is β-sulfoethyl, 2-, 3- or 4-sulfophenyl in which the phenyl ring can be substituted by methyl, methoxy, chlorine, acetylamino and carboxyl, 2,5-disulfophenyl, monosulfonaphthyl or disulfonaphthyl, X is hydrogen, methyl, chlorine, ethoxy, acetylamino or phenoxy, and Y is hydrogen, chlorine or methoxy.

In particularly preferred monoazo dyes of the formula (1), K is an N,N-di-$C_{1-4}$-alkylaminobenzene radical which can be substituted in the benzene nucleus by methyl, chlorine, acetylamino and benzoylamino and in which the N-alkyl radicals can be substituted independently of each other by hydroxyl, chlorine, cyano, phenyl or sulfophenyl, a 1-phenyl-3-methylaminopyrazole radical which can be substituted in the phenyl radical by chlorine and sulfo, or a 2-methylindole or 1-ethyl-2-methylindole radical, and R, X and Y are as defined above.

In especially preferred monoazo dyes of the formula (1), K is an N,N-diethyl-3-methylaniline radical, an N-ethyl-N-β-hydroxyethyl-3-methylaniline radical, a 1-phenyl-3-methyl-5-aminopyrazole radical or a 2-methylindole radical, R is a β-sulfoethylaminosulfonyl, o-sulfophenylaminosulfonyl, p-sulfophenylaminosulfonyl, p-sulfophenylaminocarbonyl or p-methyl-m-sulfobenzoyl radical, X is methyl or chlorine, and Y is hydrogen.

The invention also relates to a process for preparing monoazo dyes of the formula (1). The process comprises diazotising a diazo component of the formula

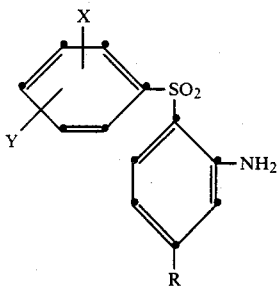

and coupling it onto a coupling component of the formula

H—K  (5), where K, R, X and Y in the formulae (4) and (5) are as defined under the formula (1).

The diazo component of the formula (4) is generally diazotised through the action of nitrous acid in an aqueous mineral acid solution at a low temperature, and the diazotisation product is coupled onto the coupling component of the formula (5) at acid, neutral to alkaline pH values.

If desired, after the coupling, a free amino group in the radical K can be converted into an acylamino or alkylamino-group, by means of an acylating or alkylating agent, and, similarly, a hydroxyl group in the radical K can be alkylated to give an alkoxy group.

Those azo dyes of the formula (1) which contain a fibre-reactive radical are prepared by reacting with one another in any order a diazo component of the formula (4), a formula (5) coupling component which contains an acylatable amino or hydroxyl group, and an acylating agent which contains a fibre-reactive radical.

The coupling components used as containing an acylatable group are preferably of the benzene or naphthalene series.

Preferred versions of the process comprise (a) using a coupling component of the formula (5) in which K is the radical of an aminobenzene, alkoxybenzene, aminonaphthalene, alkoxynaphthalene, naphthol, aminonaphthol, pyrazolone, aminopyrazole, pyridone, pyrimidine, indole, naphthimidazole, diphenylamine, pyrazolo[2,3-a]pyrimidine, tetrahydroquinoline or acetoacetamide, which radicals can be further substituted, (b) using a diazo component of the formula (4) in which $R_2$ is an unsubstituted monosulfo-$C_{1-12}$-alkyl radical, a radical of the formula

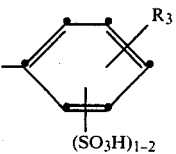

or a radical of the formula

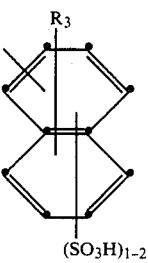

in which $R_3$ in the formulae (2) and (3) is hydrogen, $C_{1-4}$-alkyl, $C_{1-4}$-alkoxy, halogen, $C_{2-6}$-alkanoylamino or carboxyl, (c) using a diazo component of the formula (4) in which Y is hydrogen, chlorine or methoxy, or (d) using a diazo component of the formula (4) in which X is bonded to the phenyl ring in p-position relative to the —SO$_2$ group.

The particularly preferred monoazo dyes of the formula (1) are prepared by diazotising a diazo component of the formula (4) in which R is a

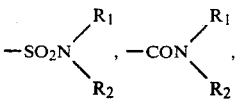

—CO—$R_2$ or —SO$_2$—O—$R_2$ group
in which $R_1$ is hydrogen or methyl, and $R_2$ is β-sulfoethyl, 2-, 3- or 4-sulfophenyl in which the phenyl ring can be substituted by methyl, methoxy, chlorine, acetylamino and carboxyl, 2,5-disulfophenyl or monosulfonaphthyl or disulfonaphthyl, and in which X is hydrogen, methyl, chlorine, ethoxy, acetylamino or phenoxy, and Y is hydrogen, chlorine or methoxy, and coupling the diazotisation product onto a coupling component of the formula (5) in which K is an N-$C_{1-4}$-alkylaminobenzene or N,N-di-$C_{1-4}$-alkylaminobenzene radical which can be substituted in the benzene ring by methyl, chlorine, acetylamino and benzoylamino and in which the N-alkyl radicals can be substituted independently of each other by hydroxyl, chlorine, cyano, phenyl or sulfophenyl, a methoxybenzene radical, a methoxynaphthalene radical, an aminonaphthalene radical which can be substituted by sulfo, a hydroxynaphthalene radical which can be substituted by sulfo, an aminonaphthol radical which can be substituted in the naphthalene nucleus by sulfo, and in which the amino group can be substituted by methyl, α,β-dibromopropionyl, α,β-dibromopropionylaminobenzoyl and 2,6-difluoro-5-chloropyrimidylaminobenzoyl, a 1-phenyl-3-methylpyrazolone radical which can be substituted in the phenyl radical by chlorine and methyl, a 1-phenyl-3-methylaminopyrazole radical which can be substituted in the phenyl radical by chlorine and sulfo, a 1-ethyl-4-methyl-6-hydroxypyrid-2-one radical which can be substituted in the 3-position by carbamoyl, a 2,4,6-triaminopyrimidine radical, a 2-methylindole of 1-ethyl-2-methylindole radical, a 1-chlorophenylamino-2-methylnaphthimidazole or 2-pentylnaphthimidazole radical which can be substituted in the naphthalene nucleus by hydroxyl and sulfo, an N-methyl or N-ethyl-1,2,3,4-tetrahydroquinoline radical, or a 2,5-dimethyl-7-aminopyrazolo[2,3-a]pyrimidine radical.

Use is made in particular of a coupling component of the formula (5) in which K is an N,N-di-$C_{1-4}$-alkylaminobenzene radical which can be substituted in the benzene nucleus by methyl, chlorine, acetylamino and benzoylamino and in which the N-alkyl radicals can be substituted independently of one another by hydroxyl, chlorine, cyano, phenyl or sulfophenyl, a 1-phenyl-3-methylaminopyrazole radical which can be substituted in the phenyl radical by chlorine and sulfo, or a 2-methylindole or 1-ethyl-2-methylindole radical.

The especially preferred monoazo dyes of the formula (1) are prepared by diazotising a diazo component of the formula (4) in which R is a $\beta$-sulfoethylaminosulfonyl, o-sulfophenylaminosulfonyl, p-sulfophenylaminosulfonyl, p-sulfophenylaminocarbonyl or p-methyl-m-sulfobenzoyl radical, X is methyl or chlorine, and Y is hydrogen, and coupling the diazotisation product onto a coupling component of the formula (5) in which K is an N,N-diethyl-3-methylaniline radical, an N-methyl-N-$\beta$-hydroxyethyl-3-methylaniline radical, a 1-phenyl-3-methyl-5-aminopyrazole radical or a 2-methylindole radical.

The following are mentioned as examples from the large number of possible coupling components: aniline, dimethylaniline, diethylaniline, 3-methyldimethylaniline, 3-methyldibutylaniline, 3-methyldiethylaniline, 3-acetylaminodimethylaniline, 3-methoxycarbonylaminodimethylaniline, 3-ureidodimethylaniline, 3-methyl-6-methoxydiethylaniline, 3-methyl-N-ethyl-N-butylaniline, 2,5-dimethoxydiethylaniline, N-ethyl-N-benzylaniline, N-ethyl-N-($\beta$-cyanoethyl)-aniline, N-ethyl-N-($\beta$-hydroxyethyl)-aniline, N-ethyl-N-($\beta$-acetoxyethyl)-aniline, N,N-dibutylaniline, 3-acetylamino-N,N-diethylaniline, N-methyl-N-($\beta$-cyanoethyl)-aniline, 3-methyl-N,N-di-($\beta$-cyanoethyl)-aniline, 3-chloro-N,N-dimethylaniline, 3-methyl-N-ethyl-N-benzylaniline, N,N-di-n-propylaniline, 3-acetylamino-N,N-di-($\beta$-hydroxyethyl)-aniline, 3-methyl-N,N-di-($\beta$-acetoxyethyl)-aniline, 3-methyl-N-ethyl-N-(3'-sulfobenzyl)-aniline, N-ethyl-N-($\beta$-chloroethyl)-aniline, 2-methoxy-5-acetylamino-N-benzylaniline, 2-methoxy-5-acetylamino-N-($\beta$-acetoxyethyl)-N-benzylaniline, 3-methyl-N,N-dibutylaniline, 3-methyl-N-ethyl-N-($\beta$-cyanoethyl)-aniline, 2-methyl-5-acetylamino-N,N-dimethylaniline, 2-chloro-5-acetylamino-N,N-dimethylaniline, 2-chloro-5-acetylamino-N-($\gamma$-phenoxy-$\beta$-hydroxy-n-propyl)-aniline, 3-ureidoaniline, N-ethyl-N-($\beta$-hydroxyethyl)-aniline, N-ethyl-N-(3'-sulfobenzyl)-aniline, 3-methyl-N-ethyl-N-($\beta$-sulfoethyl)-aniline, 3-benzoylamino-N,N-diethylaniline, 3-(p-tolylsulfamoyl)-N,N-diethylaniline, 3-(p-chlorobenzoylamino)-N,N-diethylaniline, 3-methoxy-N,N-diethylaniline, 3-methyl-N,N-di-($\beta$-hydroxyethyl)-aniline, 3-methyl-6-methoxy-N,N-di($\beta$-hydroxyethyl)-aniline, 3-acetylaminoaniline, 3-methyl-N-ethyl-N-phenethylaniline, N,N-di-($\beta$-cyano- or hydroxyethyl)-aniline, 3-acetylamino-N,N-di-($\beta$-cyanoethyl)-aniline, 3-methyl-N-ethyl-N-($\beta$-hydroxyethyl)-aniline, 3-methyl-N-ethyl-N-($\beta$-hydroxyethyl)-aniline, N-($\beta$-cyanoethyl)-aniline, N-methyl-N-benzylaniline, phenol, 3-methylphenol, methoxybenzene, 3-ethoxytoluene, 1-hydroxy-4-methoxybenzene, 1-hydroxy-4-tert.-butylbenzene, 1-hydroxy-7-amino-3-sulfonaphthalene, 1-hydroxy-7-methylaminosulfonaphthaline, 7-phenylamino-3-sulfonaphthalene, 2-aminonaphthalene, 2-amino-6-sulfonaphthalene, 2-amino-5-acetylaminomethylnaphthalene, $\beta$-naphthol, 2-amino-5-methylaminosulfonylnaphthalene, 1-hydroxy-8-amino-3,6-disulfonaphthalene, 1-hydroxy-8-amino-3,5-disulfonaphthalene, 1-hydroxy-8-benzoylamino-3,6-disulfonaphthalene, 1-hydroxy-8-benzoylamino-3,5-disulfonaphthalene, 1-hydroxy-8-ureido-3,6-disulfonaphthalene, 1-hydroxy-8-ureido-3,5-disulfonaphthalene, 1-hydroxy-8-acetylamino-3,6-disulfonaphthalene, 1-hydroxy-8-ureido-3,5-disulfonaphthalene, 1-(3'-chlorophenyl)-3-methylpyrazol-5-one, 1-(2'-chloro-6'-methylphenyl)-3-methylpyrazol-5-one, 1-phenyl-3-methylpyrazol-5-one, 1-(2',3'- or 4'-sulfophenyl)-3-methylpyrazol-5-one, 1-(2'-chloro-4'- or 5',-sulfophenyl)-3-methylpyrazol-5-one, 1-(3'- or 4'-dibromopropionylamino)-benzoylamino-8-hydroxy-3,6-disulfonaphthalene, 1-(3'- or 4'-dibromopropionylamino)-benzoylamino-8-hydroxy-4,6-disulfonaphthalene, 2-$\alpha,\beta$-dibromopropionylamino-1-hydroxy-6-sulfonaphthalene, 3-$\alpha,\beta$-dibromopropionyl-N-methylamino-8-hydroxy-6-sulfonaphthalene, 1-[3'-(2'',4''-difluoro-5'-chloropyrimidylamino)-benzoylamino]-8-hydroxy-4,6-disulfonaphthalene, 1-(2'-methyl-4'-sulfophenyl)-3-methylpyrazol-5-one, 1-[4',8'-disulfonaphth-2-yl]-3-methylpyrazol-5-one, 1-[5',7'-disulfonaphthal-2-ene]-3-methylpyrazol-5-one, 1-(2'-chloro-5'-sulfophenyl)-3-methyl-5-aminopyrazole, 1-(2'-chloro-4'-sulfophenyl)-3-methyl-5-aminopyrazole, 1-(3'- or 4'-sulfophenyl)-3-methyl-5-aminopyrazole, 1-ethyl-3-cyano-4-methyl-6-hydroxypyrid-2-one, 1-ethyl-3-carbamoyl-4-methyl-6-hydroxypyrid-2-one, 1-ethyl-4-methyl-6-hydroxypyrid-2-one, 1-ethyl-4-methyl-3-methylsulfonyl-6-hydroxypyrid-2-one, 2-methylindole, 2-phenylindole, 1-methyl-2-phenylindole, 1-octyl-2-methylindole, 2,4,6-triaminopyrimidine, N-methyl-N,N-diphenylamine, acetoacetanilide, 1-(4'-methylphenyl)-3-methylpyrazol-5-one, 1-ethyl-2-methylindole, 1-phenyl-3-methyl-5-aminopyrazole, 7-amino-2,5-dimethylpyrazol[2,3-a]pyrimidine, 1-methoxynaphthalene, 1-hydroxy-4-sulfonaphthalene, 1-(2'-chlorophenylamino)-9-hydroxy-2-methyl-1H-naphtho(1,2-d)imidazole-7-sulfonic acid, 1-(2'-chlorophenylamino)-9-hydroxy-2-pentyl-1H-naphtho(1,2-d)imidazole-7-sulfonic acid, N-methyl-1,2,3,4-tetrahydroquinoline, N-ethyl-1,2,3,4-tetrahydroquinoline, 3-methyl-N-ethyl-N-propylaniline.

The present invention also relates to compounds which are used as diazo components and have the formula

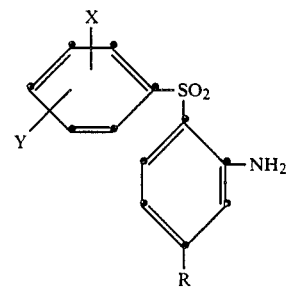

(4)

in which R, X and Y are as defined under the formula (1).

In preferred compounds of the formula (4), R is a

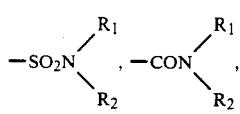

—CO—$R_2$ or —$SO_2$—O—$R_2$ group in which $R_1$ is hydrogen or $C_{1-4}$-alkyl and $R_2$ is an unsubstituted monosulfo-$C_{1-12}$-alkyl radical, a radical of the formula

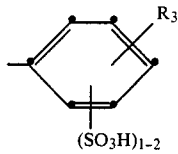

or a radical of the formula

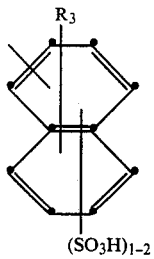

in which $R_3$ in the formulae (2) and (3) is hydrogen, $C_{1-4}$-alkyl, $C_{1-4}$-alkoxy, halogen, $C_{2-6}$-alkanoylamino or carboxyl, and X and Y are as defined under formula (1).

In likewise preferred compounds of the formula (4),
(a) Y is hydrogen, chlorine or methoxy, and
(b) X is bonded to the phenyl ring in p-position relative to the —$SO_2$ group.

In particular preferred compounds of the formula (4), R is a

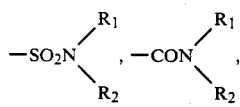

—CO—$R_2$ or —$SO_2$O—$R_2$ group in which $R_1$ is hydrogen or methyl, $R_2$ is β-sulfoethyl, 2-, 3- or 4-sulfophenyl in which the phenyl ring can be substituted by methyl, methoxy, chlorine, acetylamino and carboxyl, 2,5-disulfophenyl, monosulfonaphthyl or disulfonaphthyl, X is hydrogen, methyl, chlorine, ethoxy, acetylamino or phenoxy, and Y is hydrogen, chlorine or methoxy.

In especially preferred compounds of the formula (4), R is a β-sulfoethylaminosulfonyl, o-sulfophenylaminosulfonyl, p-sulfophenylaminosulfonyl, p-sulfophenylaminocarbonyl or p-methyl-m-sulfobenzoyl radical, X is methyl or chlorine, and Y is hydrogen.

Compounds of the formula (4) are prepared by reacting compounds of the formula

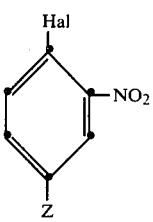

in which Z is a —$SO_2$—Hal or —CO—Hal group and Hal is halogen, with a compound of the formula

in which $R_1$ and $R_2$ are as defined under the formula (4), to give a compound of the formula

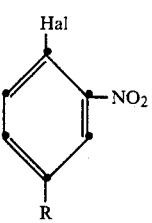

in which R is as defined under the formula (4) and Hal is halogen, condensing the compound of the formula (8) with a compound of the formula

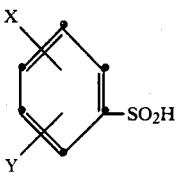

in which X and Y are as defined under the formula (4), and then reducing the $NO_2$ group.

A version of the process for preparing compounds of the formula

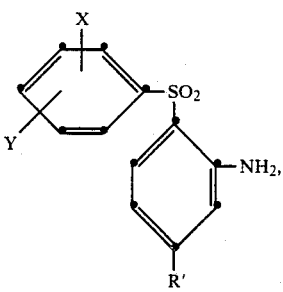

in which R' is an

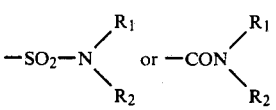

group, and $R_1$, $R_2$, X and Y are as defined under the formula (4), comprises reacting a compound of the formula

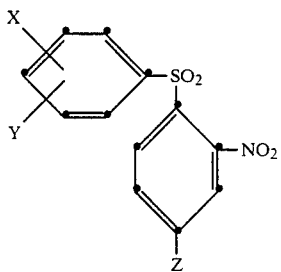

(11)

in which Z is an —SO₂—Hal or —CO—Hal group and Hal is halogen, with an amine of the formula

(12)

and then reducing the nitro group, while $R_1$, $R_2$, X and Y in the formulae (11) and (12) are as defined under the formula (10).

The ways of preparing compounds of the formula (4) are known per se. The reactions are carried out at temperatures between 0° and 150° C., if desired under pressure in an aqueous solution or mixtures of organic solvents, for example acetone and water, and at pH values between 7 and 10. The nitro group is likewise reduced by methods known per se, for example in glacial acetic acid in the presence of iron powder.

Examples which may be mentioned of starting compounds of the formula (6) are 4-chloro-3-nitrobenzoyl chloride and 4-chloro-3-nitrobenzene-1-sulfonyl chloride.

Examples which may be mentioned of starting compounds of the formula (7) are 2-, 3- or 4-sulfophenylaniline, taurine, N-methyltaurine, 2-aminonaphthalene-6-sulfonic acid, 2-aminonaphthalene-1-sulfonic acid, 2-aminonaphthalene-1,5-disulfonic acid, 2,5-disulfoaniline, 4-acetylamino-3-sulfoaniline, 2-chloro-5-sulfoaniline, 2-carboxy-4-sulfoaniline, 2-methyl-4-sulfoaniline, 2-methoxy-5-sulfoaniline, 4-methyl-3-sulfoaniline, 4-sulfophenol, 2-sulfotoluene and 2-chlorobenzenesulfonic acid.

Examples which may be mentioned of starting compounds of the formula (9) are 4-chlorobenzenesulfinic acid, benzenesulfinic acid, 4-ethoxybenzenesulfinic acid, 4-acetylaminobenzenesulfinic acid, 4-phenoxybenzenesulfinic acid, 4-bromobenzenesulfinic acid, 4-iodobenzenesulfinic acid, 2-methylbenzenesulfinic acid, 3-methylbenzenesulfinic acid, 4-methylbenzenesulfinic acid, 2,3-dimethylbenzenesulfinic acid, 3,4-dimethylbenzenesulfinic acid, 2,4-dimethylbenzenesulfinic acid, 2,5-dimethylbenzenesulfinic acid, 3,5-dimethylbenzenesulfinic acid, 2-methyl-5-isopropylbenzenesulfinic acid, 2-methoxybenzenesulfinic acid, 2-ethoxybenzenesulfinic acid, 4-methoxybenzenesulfinic acid, 2-methoxy-5-methylbenzenesulfinic acid, 2-bromo-5-methoxybenzenesulfinic acid and 2-methyl-4-chlorobenzenesulfinic acid.

Examples which may be mentioned of starting compounds of the formula (11) are 4'-chloro-, 4'-methyl-, 4'-ethoxy-, 4'-acetylamino-, 4'-H- or 4'-phenoxy-2-nitro-1,1'-diphenylsulfone-4-sulfonyl or 1-4-carbonyl chloride.

The amines mentioned for the formula (7) are examples of starting compounds of the formula (12).

Examples which may be mentioned of compounds of the formula (4) are 4'-chloro-, 4'-methyl-, 4'-ethoxy-, 4'-acetylamino- or 4'-phenoxy-2-amino-N-(β-sulfoethyl)-1,1'-diphenylsulfone-4-sulfonamide or -carboxamide, 4'-chloro-, 4'-methyl-, 4'-ethoxy, 4'-acetylamino or 4'-phenoxy-2-amino-N-(2''-, 3''- or 4''-sulfophenyl)-1,1'-diphenylsulfone-4-sulfonamide or -carboxamide, 4'-chloro-, 4'-methyl-, 4'-ethoxy-, 4'-acetylamino- or 4'-phenoxy-2-amino-N-(1''-sulfonaphth-2-yl, 6''-sulfonaphth-2-yl or 1'',5''-disulfonaphth-2-yl)-1,1'-diphenylsulfone-4-sulfonamide or carboxamide, 2-amino-N-methyl-N-(β-sulfoethyl)-1,1'-diphenylsulfone-4-sulfonamide or -carboxamide, 2-amino-N-(2''-, 3''- or 4''-sulfophenyl)-1,1'-diphenylsulfone-4-sulfonamide or carboxamide, 2-amino-N-(β-sulfoethyl)-1,1-diphenylsulfone-4-sulfonamide or -carboxamide, 2-amino-N-(1''-sulfonapth-2-yl, 6''-sulfonaphth-2-yl or 1'',5''-disulfonaphth-2-yl)-1,1'-diphenylsulfone-4-sulfonamide or -carboxamide, 2-amino-N-(4''-acetylamino-3''-sulfophenyl)-1,1'-diphenylsulfone-4-sulfonamide, 4'-methyl-2-amino-N-(2''-chloro-5''-sulfophenyl)-1,1'-diphenylsulfone-4-sulfonamide, 2-amino-N-(2''-chloro-5''-sulfophenyl)-1,1'-diphenylsulfone-4-sulfonamide, 2-amino-N-(2''-carboxy-4''-sulfophenyl)-1,1'-diphenylsulfone-4-sulfonamide, 4'-chloro-2-amino-N-(2'',5''-disulfophenyl)-1,1-diphenylsulfone-4-sulfonamide, 4'-methyl-2-amino-N-(2''-carboxy-4''-sulfophenyl)-1,1'-diphenylsulfone-4-sulfonamide, 4'-methyl-2-amino-N-(2''-methyl-4''-sulfophenyl)-1,1'-diphenylsulfone-4-sulfonamide, 2-amino-N-(2''-methyl-4''-sulfophenyl)-1,1'-diphenylsulfone-4-sulfonamide, 4'-methyl-2-amino-N-(2''-methoxy-5''-sulfophenyl)-1,1'-diphenylsulfone-4-sulfonamide, 2-amino-N-(2''-methoxy-5''-sulfophenyl)-1,1-diphenylsulfone-4-sulfonamide, 4'-methyl-2'-methoxy-2-amino-N-(3''-sulfophenyl)-1,1'-diphenylsulfone-4-sulfonamide, 2'-methoxy-2-amino-N-(3''-sulfophenyl)-1,1'-diphenylsulfone-4-sulfonamide, 4'-chloro- or 4'-methyl-2-amino-N-(2''-chloro-5''-, 2''-methyl-4''-, 2''-methoxy-5''- or 4''-acetylamino-3''-sulfophenyl)-1,1'-diphenylsulfone-4-carboxamide, 2-amino-N-(2''-chloro-5''-, 2''-methyl-4''-, 2''-methoxy-5''- or 4''-acetylamino-3''-sulfophenyl)-1,1'-diphenylsulfone-4-carboxamide, 4'-methyl-2-amino-N-(4''-sulfophenyl)-1,1'-diphenylsulfone-4-sulfonamide, 4'-acetylamino-2-amino-N-(4''-sulfophenyl)-1,1'-diphenylsulfone-4-sulfonamide, 4'-chloro- or 4'-methyl-2-amino-N-(4''-methyl-3''- or 4''-chloro-3''-sulfophenyl)-1,1'-diphenylsulfone-4-phenylcarbonyl, 2-amino-N-(4''-methyl-3''- or 4''-chloro-3''-sulfophenyl)-1,1'-diphenylsulfone-4-phenylcarbonyl, 4'-bromo-, 4'-iodo-, 2'-methyl-, 3'-methyl-, 2',3'-dimethyl-, 3',4-dimethyl-, 2',4'-dimethyl, 2',5'-dimethyl- or 3',5'-dimethyl-2-amino-N-(β-sulfoethyl or 2''-, 3''- or 4''-sulfophenyl)-1,1'-diphenylsulfone-4-sulfonamide or -carboxamide, 2'-methoxy-, 2'-ethoxy, 4'-methoxy-, 2'-methoxy-5'-methyl-, 2'-bromo-5'-methoxy or 2'-methyl-4'-chloro-2-amino-N-(2''-chloro-5''-, 2''-methyl-4''-, 2''-methoxy-5''- or 4''-acetylamino-3''-sulfophenyl)-1,1-diphenylsulfone-4-sulfonamide or -carboxamide.

The dyes used in the invention are either in the form of their free sulfonic acid or, preferably, in the form of its salts.

Examples of possible salts are the alkali metal, alkaline earth metal or ammonium salts or of the salts of an organic amine. Examples which may be mentioned are the sodium, lithium, potassium or ammonium salts or the salt of triethanolamine.

Dyes of the formula (1) are suitable for dyeing and printing materials containing amide groups, such as textile fibres and textile yarns and fabrics made of wool, silk and polyurethane fibres, but in particular for dyeing and printing synthetic polyamide, for which the customary dyeing methods are used.

They are distinguished by brilliance and tinctorial strength, and good affinity and build-up and they produce dyeings of generally good fastness properties, such as fastness to rubbing, acids and alkalis, and wet fastness properties, in particular fastness to washing, water, hot water and perspiration, and they produce level dyeings. It is particularly noteworthy that the light fastness is very good and that the resistance to formaldehyde is very good.

In the following examples the parts are parts by weight. The temperatures are in degree centrigrade. Parts by weight relate to parts by volume as the gramme relates to the cubic centimeter.

EXAMPLE 1

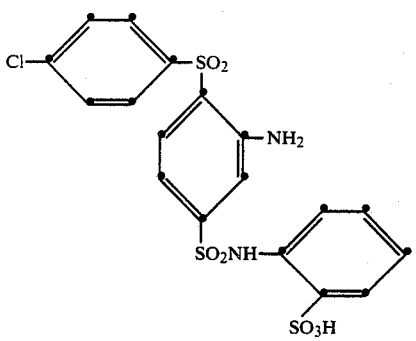

81.6 g of aniline-2-sulfonic acid (84.9% pure) are dissolved at room temperature in 400 ml of water and brought to pH 9 by adding 10N sodium hydroxide solution. 123.4 g of 4-chloro-3-nitrobenzene-1-sulfonyl chloride (82.9% pure) are added, and the reaction mixture is stirred at room temperature for 28 hours while pH 9 is maintained by means of 10N sodium hydroxide solution. After a further 2 hours, at 45°–50°, the turbid solution at pH 9 is clarified with active charcoal and is then brought to pH 7 by means of concentrated hydrochloric acid, and the precipitated product is filtered off at 30°, is washed with 250 ml of water and is dried in a vacuum cabinet at 60°–70°. The yield is 134.9 g.

131.5 g of this compound are stirred together with 96.0 g of sodium 4-chlorobenzenesulfinate (68.8% pure) into 1,000 ml of water, and the suspension is brought to pH 7.5 by means of dilute sodium hydroxide solution. After a dwell time of 15 hours at 112°–115° in a tantalum autoclave, the slurry is diluted at 80° with 300 ml of water and filtered. The solids content of the well-pressed filter cake is 188 g.

187 g of this material, which is nitrodiphenyl sulfone, are introduced at 94°–97° in the course of 25 minutes into 600 ml of water which contains 64 g of iron powder and 4.5 ml of glacial acetic acid. The mixture is stirred at the reflux temperature for 20 minutes and is then carefully admixed, at 90°–80°, with 5.6 g of sodium carbonate, and the iron residue is filtered off. The filtrate is brought to pH 11.8 by means of 10N sodium hydroxide solution and is clarified with active charcoal. Sodium chloride is added, the mixture is stirred for 1 hour, and the precipitate is filtered off, is washed with sodium chloride solution and is dried at 60°–70° in vacuo.

This gives, in virtually pure form, 178 g of the compound with the formula shown above.

EXAMPLE 2

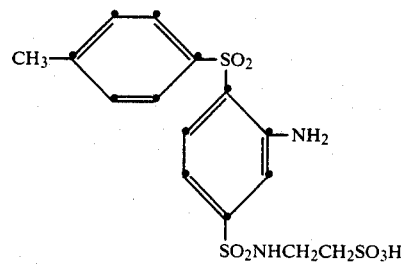

75 g of taurine are stirred into 600 ml of water, and pH 9.5 is established by means of concentrated sodium hydroxide solution. The solution is cooled down to 0°, and a solution of 203.5 g of 4-chloro-3-nitrobenzene-1-sulfonyl chloride (75.6% pure) in 200 ml of acetone is added dropwise. The pH established above is held at a constant value by means of sodium hydroxide solution, and the product precipitated on adding salt is separated off. The washed and dried product is obtained in a yield of 131.7 g.

131 g of this compound are stirred together with 57.6 g of Na toluene-4-sulfinate into 450 ml of water, and the suspension is adjusted to pH 7.5 by means of sodium carbonate. After a dwell time of 20 hours at 105°–107° in a tantalum autoclave, the slurry is turned into a solution by means of hot water. The product is salted out, is filtered, is washed and is dried at 60°–70° in vacuo. This gives 135.8 g of powder.

135 g of the nitrodiphenyl sulfone are reduced at the boil in 700 ml of water which contains 58 g of iron powder and 8 ml of glacial acetic acid. 9.8 g of sodium carbonate are carefully added, and the iron residue is filtered off. Sodium chloride is added to the filtrate, and the precipitated product is filtered off, is washed and is dried at 60°–70° in vacuo.

This gives, in a chromatographically pure form, 151.2 g of the compound with the formula shown above.

EXAMPLE 3

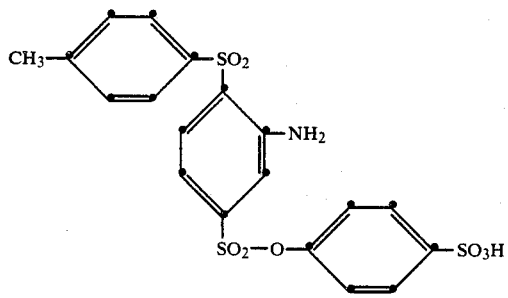

Sodium hydroxide solution is used to bring 46 g of phenol-4-sulfonic acid (75.6% pure) into solution in 300 ml of water at room temperature and bring the solution to pH 8.5. 67.2 g of 4-chloro-3-nitrobenzene-1-sulfonyl chloride (74% pure) dissolved in 100 ml of acetone are then added dropwise while the pH is maintained at a value of 8.5 by means of 10N sodium hydroxide solution. 15 hours later the precipitate is filtered off with suction and washed.

The filter cake is stirred together with 31.6 g of Na toluene-4-sulfinate (95.6% pure) into 300 ml of water, and pH 8 is established by means of sodium carbonate. After a dwell time of 20 hours at 104°–107° in a steel autoclave, the product is filtered off and washed. The moist filter cake is introduced into 250 ml of water which contains 34 g of iron powder and 3 ml of glacial acetic acid, and is reduced at the boil. 7 g of sodium carbonate are carefully added, the iron residue is filtered off, and the filtrate is evaporated to dryness. The yield is 76 g.

EXAMPLE 4

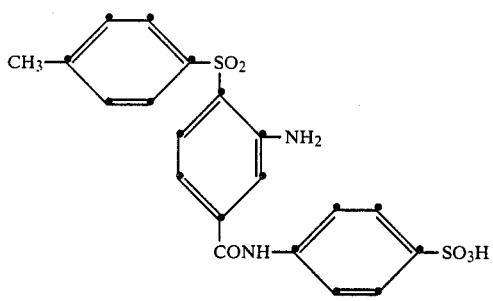

87.5 g of sulfanilic acid (99% pure) are stirred into 500 ml of water brought to pH 7–8 by means of concentrated sodium hydroxide solution, and the solution is cooled down to 5°, when 106.2 g of 4-chloro-3-nitrobenzoyl chloride dissolved in 100 ml of acetone are added dropwise. The mixture is stirred for a while at pH 7 and the carboxamide is then precipitated by adding sodium chloride. After drying in vacuo at 60°–70°, the filter from the washed product weighs 163 g. 61.2 g of this compound are left together with 30.7 g of Na toluene-4-sulfinate (95.6% pure) for some hours in 300 ml of water at reflux temperature. The filtered and washed sulfone derivative is dried at 60°–70° in vacuo to give 66.8 g of a chromatographically pure substance.

66 g of the nitrodiphenyl sulfone are reduced at the boil in 250 ml of water which contains 30 g of iron powder and 2 ml of glacial acetic acid. 3.1 g of sodium carbonate are carefully added, the iron residue is filtered off, and the pure product in the filtrate is precipitated by adding sodium chloride. It is then filtered off, washed, and dried at 60°–70° in vacuo. The yield is 62 g of the compound of the formula shown above.

EXAMPLE 5

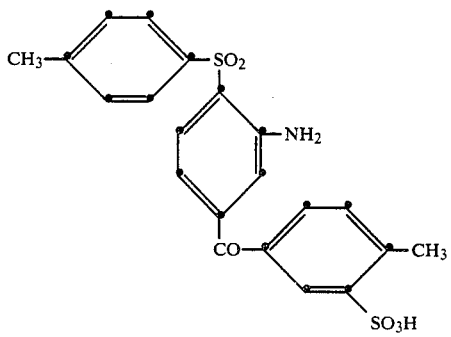

138 g of 1-chloro-2-nitro-4'-methylbenzophenone are sulfonated at 20°–48° in 450 ml of 25% oleum. The mixture is poured onto ice, and the product is precipitated with sodium chloride, is filtered off, is dissolved again in water and is salted out with potassium chloride. The precipitate is filtered off with suction, is washed and is dried at 60°–70° in vacuo. The yield is 221.4 g.

59.8 g of this compound, together with 20.46 g of Na toluene-4-sulfinate (95.6% pure), are brought to pH 8 in 300 ml of water, and are heated at the boil for some time. The sulfone derivative is filtered off cold, is washed, is added, as a moist material, to 300 ml of water which contains 20 g of iron powder and 2 ml of glacial acetic acid, and is reduced therein at the boil to give an amine. 3.1 g of sodium carbonate is carefully added, the iron residue is filtered off with suction, and the product is precipitated in the filtrate by means of sodium chloride. It is then filtered off, washed, and dried at 60°–70° in vacuo to give 49.7 g of the compound with the formula shown above.

EXAMPLE 6

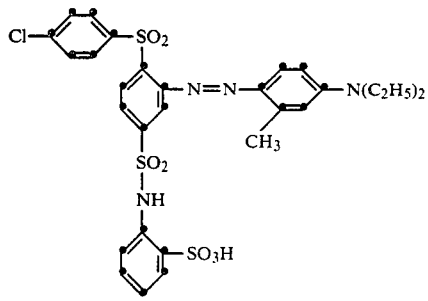

12.53 g of the compound of Example 1 (80.2% pure) are stirred into 100 ml of neutral ice-water and then admixed with 5 ml of 4N sodium nitrite. 6 ml of concentrated hydrochloric acid are added, and the suspension is left to stir for some time, and any excess nitrite is then destroyed by means of sulfamic acid.

3.26 g of N,N-diethyl-m-toluidine are emulsified in 40 ml of water which contains 2.12 g of sodium carbonate. The diazonium salt suspension prepared above is added dropwise at pH 8.5, maintained by means of sodium hydroxide solution, and the coupling product is acidified after some time with hydrochloric acid. The dye is filtered off, washed, and dried at 60°–70° in vacuo.

This gives 10.41 g of a water-soluble dye which contains sodium carbonate as a diluent and which dyes polyamide from a weakly acid bath in brilliant red shades. The dye builds up well and has superb light fastness, very good resistance to formaldehyde and good wet fastness properties.

EXAMPLE 7

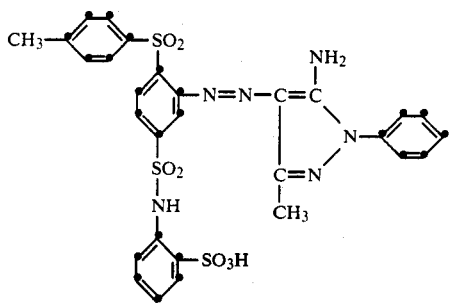

8.87 g of 2-amino-4'-methyldiphenylsulfone-4-sulfanilido-2''-sulfonic acid (81.5% pure) are suspended in 75 ml of neutral ice-water and are then admixed first with 3.75 ml of 4N sodium nitrite and then with 4.5 ml of concentrated hydrochloric acid. The suspension is stirred some more, and any slight excess of nitrite is destroyed with sulfamic acid. A solution of 2.7 g of 3-methyl-1phenyl-5-pyrazolimine (96.3% pure) in 20 ml of water and 2 ml of hydrochloric acid is then added, and the coupling reaction is allowed to go to completion at room temperature. The dye is filtered off, is dissolved in water brought to pH 8 by means of sodium hydroxide solution, and is precipitated with sodium chloride. The dye is filtered off again, is washed, and is dried at 60°-70° in vacuo.

This gives 7.51 g of a dye which dyes polyamide from a weakly acid bath in brilliant yellow shades. The dye builds up well and has good all-round fastness properties.

Example 8

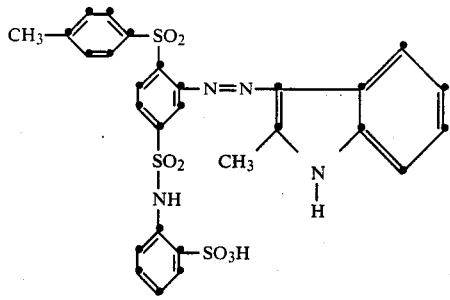

8.87 g of 2-amino-4'-methyldiphenylsulfone-4-sulfanilido-2''-sulfonic acid (81.5% pure) are diazotised as in Example 7. A solution of 1.97 g of 2-methylindole in 6 ml of concentrated hydrochloric acid is then added dropwise, and the coupling is completed at room temperature. The dye is filtered off, is dissolved in water containing sodium hydroxide solution under alkaline conditions, and is precipitated with sodium chloride. It is filtered off, washed, and dried at 60°-70° in vacuo to give 5.53 g of a dye which dyes polyamide material from a weakly acid bath in brilliant reddish yellow shades. The build-up, the light fastness and the resistance of formaldehyde and acid are very good.

Example 9

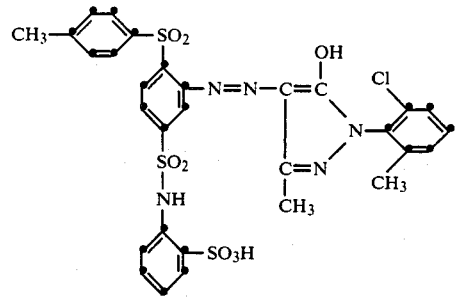

8.87 g of 2-amino-4'-methyldiphenylsulfone-4-sulfanilido-2''-sulfonic acid (81.5% pure) are diazotised as in Example 7. 6.38 g of 1-(2'-chloro-6'-methylphenyl)-3-methylpyrazol-5-one (52.4% pure) are heated to 70° in 50 ml of water containing 8 ml of 2N sodium hydroxide solution, and the mixture is clarified. The filtrate is cooled down to 2°, and the diazonium salt suspension prepared above is added dropwise while, at the same time, the pH is kept at a constant value of approximately 9 by means of 2N sodium hydroxide solution. The dye is precipitated with potassium chloride, is filtered off, is washed and is dried at 60°-70° in vacuo.

This gives 8.5 g of a dye which dyes polyamide material from a weakly acid bath in brilliant reddish yellow shades and has good all-round fastness properties.

Example 10

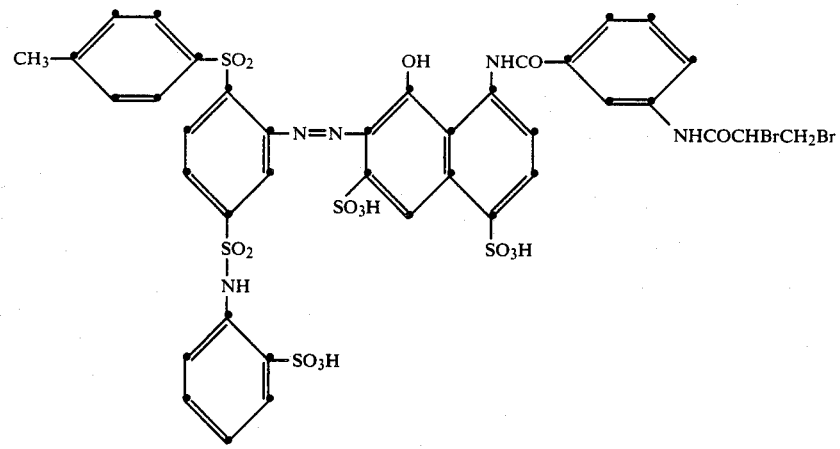

8.87 g of 2-amino-4'-methyldiphenylsulfone-4-sulfanilido-2''-sulfonic acid (81.5% pure) are diazotised as in Example 7. 17.84 g of 3-α,β-dibromopropionylaminoenzoyl-K-acid (55.1% pure) are dissolved in 80 ml of water at pH 7, and the solution is cooled down to 2°. The diazo suspension is added dropwise while the pH is kept at a constant value of 7 by means of sodium hydroxide solution. The dye is salted out with potassium chloride, is filtered off with suction and is dried at 60°–70° in vacuo. The yield is 14.3 g.

The method of Examples 1 to 10 is repeated, except that a compound of the formula

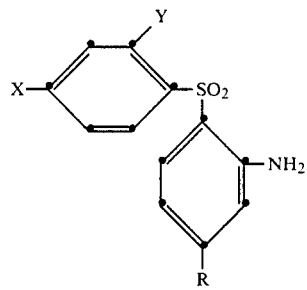

is used as diazo component and the compounds listed in the table below are used as coupling component, affording likewise valuable dyes which have similar, good properties and which dye polyamide or wool in the indicated shade.

TABLE

| Example | Diazo component Y | Diazo component X | Diazo component R | Coupling component | Shade on polyamide |
|---|---|---|---|---|---|
| 1 | H | —CH₃ | —SO₂NHCH₂CH₂SO₃H | ![structure: pyridone with CH₃, CONH₂, HO, N-C₂H₅] | greenish yellow |
| 2 | H | —CH₃ | —SO₂NHCH₂CH₂SO₃H | ![structure: phenyl with N(C₂H₅)₂ and NHCOCH₃] | red |
| 3 | H | —CH₃ | —SO₂NHCH₂CH₂SO₃H | ![structure: phenyl with N(C₂H₅)₂] | yellowish red |
| 4 | H | —CH₃ | —SO₂NHCH₂CH₂SO₃H | ![structure: N(C₂H₅)(CH₂-phenyl) on tolyl] | yellowish red |
| 5 | H | —CH₃ | —SO₂NHCH₂CH₂SO₃H | ![structure: phenyl with N(CH₃)₂ and Cl] | reddish orange |
| 6 | H | —CH₃ | —SO₂NHCH₂CH₂SO₃H | ![structure: phenyl with N(C₂H₅)₂ and CH₃] | red |

TABLE-continued

| Example | Diazo component Y | X | R | Coupling component | |
|---|---|---|---|---|---|
| 7 | H | —CH$_3$ | —SO$_2$NHCH$_2$CH$_2$SO$_3$H | phenyl-N(C$_2$H$_4$CN)$_2$ | yellowish red |
| 8 | H | —CH$_3$ | —SO$_2$NHCH$_2$CH$_2$SO$_3$H | phenyl-N(C$_2$H$_5$)(CH$_2$-phenyl) | reddish orange |
| 9 | H | —CH$_3$ | —SO$_2$NHCH$_2$CH$_2$SO$_3$H | phenyl-N(C$_2$H$_5$)(CH$_2$-phenyl-SO$_3$H) | reddish orange |
| 10 | H | —CH$_3$ | —SO$_2$NHCH$_2$CH$_2$SO$_3$H | phenyl with N(C$_2$H$_4$OH)$_2$ and NHCOCH$_3$ | red |
| 11 | H | —CH$_3$ | —SO$_2$NHCH$_2$CH$_2$SO$_3$H | phenyl with N(CH$_3$)$_2$ and CH$_3$ | red |
| 12 | H | —CH$_3$ | —SO$_2$NHCH$_2$CH$_2$SO$_3$H | indole (CH$_3$, N—H) | reddish yellow |

TABLE-continued

| Example | Diazo component Y | X | R | Coupling component | |
|---|---|---|---|---|---|
| 13 | H | —CH₃ | —SO₂NHCH₂CH₂SO₃H | [4-methylphenyl group attached to N of a 5-membered ring with O=C—CH₂ and C(CH₃)=N] | reddish yellow |
| 14 | H | —CH₃ | —SO₂NCH₂CH₂SO₃H (N—CH₃) | [3-methylphenyl with N(C₂H₅)₂] | red |
| 15 | H | —CH₃ | —SO₂NCH₂CH₂SO₃H (N—CH₃) | [naphthyl-NH- with CH₃] | reddish yellow |
| 16 | H | —H | —SO₂NHCH₂CH₂SO₃H | [3-methylphenyl with N(C₂H₅)₂] | red |
| 17 | H | —Cl | —SO₂NHCH₂CH₂SO₃H | " | red |
| 18 | H | C₂H₅O— | —SO₂NHCH₂CH₂SO₃H | " | red |
| 19 | H | —NHCOCH₃ | —SO₂NHCH₂CH₂SO₃H | " | red |
| 20 | H | —CH₃ | [phenyl-SO₂—O—phenyl-SO₃H] | [3-methylphenyl with N(C₂H₅)₂] | red |

TABLE-continued

| Example | Diazo component Y | Diazo component X | R | Coupling component | |
|---|---|---|---|---|---|
| 21 | H | —CH₃ | " | 3-methylphenyl-N(C₂H₅)(CH₂-C₆H₄-SO₃H) | yellowish red |
| 22 | H | —CH₃ | " | 2,6-diamino-4-methylpyrimidine | reddish yellow |
| 23 | H | —CH₃ | " | 1-(2-chloro-5-sulfophenyl)-3-methyl-5-pyrazolone (NH=C(CH₃)-CH₂-C(CH₃)=N) | greenish yellow |
| 24 | H | —NHCOCH₃ | " | 3-methyl-N,N-diethylaniline | red |
| 25 | H | —NHCOCH₃ | 2-SO₃H-phenyl-SO₂NH— | " | red |
| 26 | H | —H | " | " | red |
| 27 | H | —CH₃ | " | " | red |

TABLE-continued

| Example | Diazo component Y | X | R | Coupling component | Color |
|---|---|---|---|---|---|
| 28 | H | —Cl | ![benzene with SO₃H and —SO₂NH—] | " | red |
| 29 | H | —H | " | " | red |
| 30 | H | —CH₃ | " | " | red |
| 31 | H | —Cl | ![benzene with SO₃H and —SO₂NH—] (para) | " | red |
| 32 | H | —H | " | " | red |
| 33 | H | —CH₃ | " | " | red |
| 34 | H | —CH₃ | " | " | red |
| 35 | H | —CH₃ | " | ![indole with CH₃ and N—H] | reddish yellow |
| 36 | H | —CH₃ | " | ![indole with CH₃ and N—C₂H₅] | reddish yellow |
| 37 | H | —NHCOCH₃ | ![benzene with SO₃H and —SO₂NH—] | " | reddish yellow |

TABLE-continued
| Example | Diazo component Y | X | R | Coupling component | |
|---|---|---|---|---|---|
| 38 | H | —CH$_3$ | " | 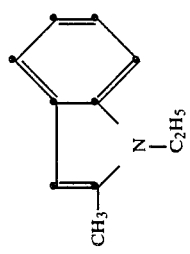 | reddish yellow |
| 39 | H | —NHCOCH$_3$ | " | 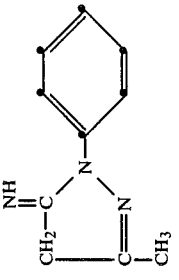 | yellow |
| 40 | H | —CH$_3$ | " | 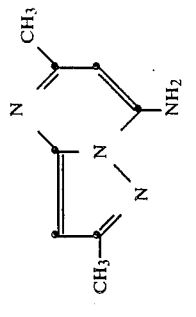 | yellow |
| 41 | H | —CH$_3$ | " | 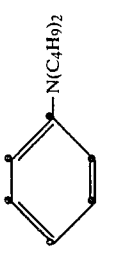 | yellowish red |
| 42 | H | —Cl | —SO$_2$NH—⌬—SO$_3$H | 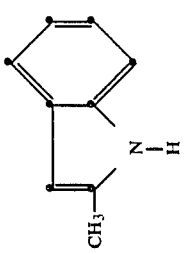 | reddish yellow |

TABLE-continued
| Example | Diazo component Y | Diazo component X | Diazo component R | Coupling component | |
|---|---|---|---|---|---|
| 43 | H | —Cl | " | 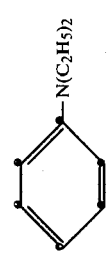 | yellow |
| 44 | H | —Cl | " | 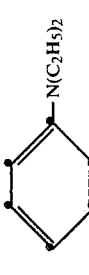 N(C₂H₅)₂ | yellowish red |
| 45 | H | —Cl | " | N(C₂H₅)₂ / NHCOCH₃ | red |
| 46 | H | —Cl | " | N(CH₃)₂ / CH₃ | red |
| 47 | H | —Cl |  SO₃H / —SO₂NH— |  CH₃ N—H | reddish yellow |
| 48 | H | —Cl | 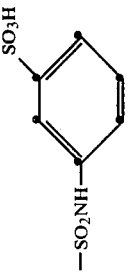 SO₃H / —SO₂NH— | " | reddish yellow |
| 49 | H | —H | " | " | reddish yellow |

TABLE-continued

| | Diazo component | | | Coupling component | |
|---|---|---|---|---|---|
| Example | Y | X | R | | |
| 50 | H | —H | [phenyl with SO₃H and —SO₂NH—] | " | reddish yellow |
| 51 | H | —H | [phenyl with SO₃H and —SO₂NH—] | " | reddish yellow |
| 52 | H | —CH₃ | [phenyl with SO₃H and —SO₂NH—] | " | reddish yellow |
| 53 | H | —CH₃ | [phenyl with SO₃H and —SO₂NH—] | [pyrazolone: NH=C(CH₂)–N(phenyl)–N=C(CH₃)] | yellow |
| 54 | H | Cl | [phenyl with SO₃H and —SO₂—NH—] | [N(C₂H₅)(CH₂-phenyl)-(tolyl-CH₃)] | yellowish red |
| 55 | H | Cl | " | [phenyl–OCH₃*] | yellowish orange |

TABLE-continued

| Example | Diazo component | | | Coupling component | |
|---|---|---|---|---|---|
| | Y | X | R | | |
| 56 | H | Cl | " | 1-methoxynaphthalene (OCH₃*) | orange |
| 57 | H | Cl | " | N(C₂H₄CN)₂, CH₃-phenyl | reddish orange |
| 58 | H | Cl | " | N(C₂H₅)(CH₂-C₆H₄-SO₃H)(C₆H₄-CH₃) | yellowish red |
| 59 | H | phenoxy-phenyl-SO₂NH-, SO₃H | " | " | yellowish red |
| 60 | H | —Cl | " | 2-amino-6-hydroxynaphthalene-HO₃S | red |
| 61 | H | —Cl | " | 2-amino-naphthol-HO₃S (NH₂, OH) | violet |

TABLE-continued

| Example | Diazo component | | | Coupling component | |
|---|---|---|---|---|---|
| | Y | X | R | | |
| 62 | H | —Cl | " | [naphthalene with OH and SO₃H] | brown |
| 63 | H | —CH₃ | " | [phenyl-N(C₂H₅)₂] | yellowish red |
| 64 | H | —CH₃ | " | [CH₃, C=O, OH, N-C₂H₅ structure] | greenish yellow |
| 65 | H | —CH₃ | " | [pyrimidine with NH₂, NH₂, NH₂] | reddish yellow |
| 66 | H | —CH₃ | " | [phenyl with N(C₂H₄CN)₂ and CH₃] | reddish orange |

TABLE-continued
| Example | Diazo component | | | Coupling component | |
|---|---|---|---|---|---|
| | Y | X | R | | |
| 67 | H | —CH$_3$ | 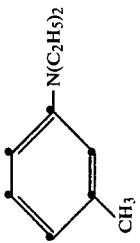 | 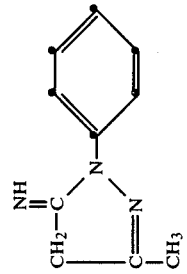 | red |
| 68 | H | —CH$_3$ | " | | yellow |
| 69 | H | —CH$_3$ | " | 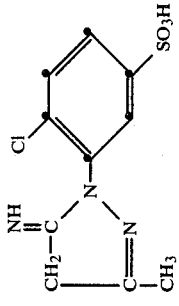 | yellow |
| 70 | H | —CH$_3$ | " | 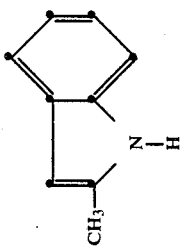 | reddish yellow |
| 71 | H | —H | " | 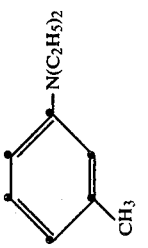 | red |
| 72 | H | —Cl | " | " | red |

TABLE-continued

| Example | Diazo component Y | Diazo component X | R | Coupling component | |
|---|---|---|---|---|---|
| 73 | H | —Cl | " | [phenyl-pyrazolone structure with NH—C(CH₂)=N—C(CH₃)=N] | yellow |
| 74 | H | —H | " | " | yellow |
| 75 | H | —H | " | [Cl, SO₃H-substituted phenyl-pyrazolone structure] | yellow |
| 76 | H | CH₃ | " | [N(C₂H₅)(CH₂-tolyl) substituted phenyl with SO₃H] | yellowish red |
| 77 | H | —CH₃ | [naphthalene with SO₃H and —SO₂NH—] | [N(C₂H₅)₂ substituted tolyl] | red |
| 78 | H | —CH₃ | " | [N(C₂H₅)(C₄H₉) substituted tolyl] | red |

TABLE-continued
| Example | Diazo component | | R | Coupling component | |
|---|---|---|---|---|---|
| | Y | X | | | |
| 79 | H | —CH$_3$ | " | 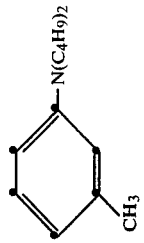 | red |
| 80 | H | —H | " | | red |
| 81 | H | —CH$_3$ | naphthalene with SO$_3$H, SO$_3$H, SO$_2$NH— | 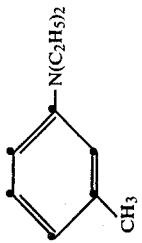 | red |
| 82 | H | —CH$_3$ | " | 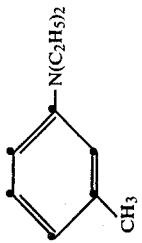 | red |
| 83 | H | —CH$_3$ | " | 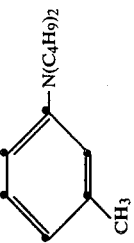 | bluish red |
| 84 | H | —CH$_3$ | " | 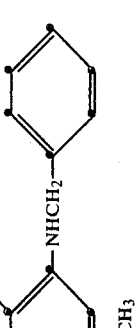 | red |

TABLE-continued

| Example | Diazo component Y | Diazo component X | R | Coupling component | Color |
|---|---|---|---|---|---|
| 85 | H | —CH₃ | " | pyrazolone derivative (NH, CH₂–C=N, N, C–CH₃ ring with N-phenyl) | yellow |
| 86 | H | —CH₃ | " | indole/carbazole-type structure with CH₃ and N—H | reddish yellow |
| 87 | H | —CH₃ | " | N(C₂H₅)(CH₂-C₆H₅) on phenyl with m-CH₃ | yellowish red |
| 88 | H | —Cl | " | 3-methyl-N,N-diethylaniline [N(C₂H₅)₂, CH₃] | red |
| 89 | H | —H | " | " | red |
| 90 | H | —H | " | 3-methyl-N,N-dibutylaniline [N(C₄H₉)₂, CH₃] | red |
| 91 | H | —Cl | " | " | red |

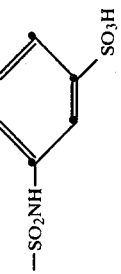

TABLE-continued
| Example | Diazo component Y | X | R | Coupling component | |
|---|---|---|---|---|---|
| 100 | H | —Cl | 4-SO₃H, 2-(—SO₂NH—phenyl-3-COOH) | | red |
| 101 | H | —CH₃ | 4-SO₃H, 2-(—SO₂NH—phenyl-3-COOH) | " | red |
| 102 | H | —CH₃ | 4-SO₃H, 2-(—SO₂NH—phenyl-3-CH₃) | " | red |
| 103 | H | —H | " | " | red |
| 104 | H | —H | 4-SO₃H, 2-(—SO₂NH—phenyl-3-OCH₃) | " | red |
| 105 | H | —CH₃ | " | 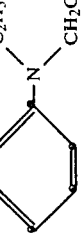 | red |
| 106 | H | —Cl | 2-SO₃H, 5-(—SO₂NH—phenyl-2-SO₃H) | | red |
| 107 | H | —Cl | " | 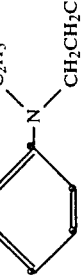 | yellowish red |

TABLE-continued

| Example | Diazo component | | | Coupling component | |
|---|---|---|---|---|---|
| | Y | X | R | | |
| 108 | H | —CH₃ | naphthalene with SO₃H and —SO₂NH— | N,N-(C₂H₅)(CH₂CH₂OH)-m-tolyl | red |
| 109 | H | —CH₃ | —SO₂NHCH₂CH₂SO₃H | 2-chlorophenyl-NH-N=C(CH₃)- coupled to 1-hydroxy-naphthalene-SO₃H | red |
| 110 | H | —CH₃ | —SO₂NHCH₂CH₂SO₃H | 2-chlorophenyl-NH-N=C(CH₂)₄CH₃- coupled to 1-hydroxy-naphthalene-SO₃H | red |
| 111 | H | —CH₃ | 4-(SO₃H)-phenyl-SO₂NH— | " | red |

TABLE-continued

| Example | Diazo component | | | Coupling component | |
|---|---|---|---|---|---|
| | Y | X | R | | |
| 112 | —OCH₃ | —CH₃ | 3-SO₂NH—C₆H₃(2-SO₃H)— | 4-CH₃-2-N(C₂H₅)₂-C₆H₃— | red |
| 113 | —OCH₃ | —H | " | " | red |
| 114 | H | —CH₃ | 4-CONH—C₆H₃(3-SO₃H)— | 4-CH₃-2-N(C₄H₉)₂-C₆H₃— | yellowish red |
| 115 | H | —CH₃ | " | 4-CH₃-2-N(C₂H₅)₂-C₆H₃— | yellowish red |
| 116 | H | —CH₃ | " | pyrazolone (1-phenyl-3-methyl) | yellow |
| 117 | H | —CH₃ | " | 2-methylindole | reddish yellow |

TABLE-continued

| Example | Diazo component | | | Coupling component | |
|---|---|---|---|---|---|
| | Y | X | R | | |
| 118 | H | —CH₃ | " | (N-ethyl-N-benzyl-m-toluidine) | reddish orange |
| 119 | H | —CH₃ | 3-SO₃H-4-(—CONH—)benzene | N,N-diethyl-m-toluidine | yellowish red |
| 120 | H | —H | " | " | yellowish red |
| 121 | H | —Cl | " | " | yellowish red |
| 122 | H | —CH₃ | " | (2-phenyl-4-methyl-imidazoline) | yellow |
| 123 | H | —H | " | " | yellow |
| 124 | H | —Cl | " | " | yellow |
| 125 | H | —CH₃ | " | (N-methyl-indoline) | reddish yellow |
| 126 | H | —H | " | " | reddish yellow |
| 127 | H | —Cl | " | " | reddish yellow |
| 128 | H | —CH₃ | 3-SO₃H-4-(—CONH—)benzene | N,N-diethyl-m-toluidine | yellowish red |

TABLE-continued

| Example | Diazo component | | | Coupling component | |
|---|---|---|---|---|---|
| | Y | X | R | | |
| 129 | H | —H | " | (pyrazolone-N-phenyl structure) | yellowish red |
| 130 | H | —Cl | " | " | yellowish red |
| 131 | H | —CH$_3$ | " | | yellow |
| 132 | H | —H | " | (indole structure with CH$_3$, N—H) | yellow |
| 133 | H | —Cl | " | " | yellow |
| 134 | H | —CH$_3$ | " | | reddish yellow |
| 135 | H | —H | " | (phenyl-N(C$_2$H$_5$)$_2$ with CH$_3$) | reddish yellow |
| 136 | H | —Cl | " | " | reddish yellow |
| 137 | H | —CH$_3$ | —CONHCH$_2$CH$_2$SO$_3$H | | yellowish red |
| 138 | H | —CH$_3$ | —CONHCH$_2$CH$_2$SO$_3$H | (pyrazolone-N-phenyl structure) | yellow |

TABLE-continued
| | Diazo component | | | Coupling component | |
|---|---|---|---|---|---|
| Example | Y | X | R | | |
| 139 | H | —CH$_3$ | —CONHCH$_2$CH$_2$SO$_3$H | 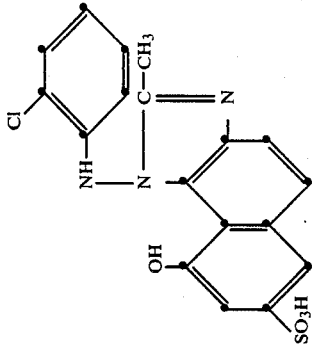 | reddish yellow |
| 140 | H | —CH$_3$ | —CONHCH$_2$CH$_2$SO$_3$H | 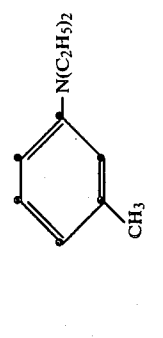 | red |
| 141 | H | —CH$_3$ | 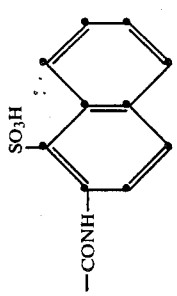 | 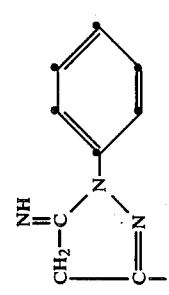 | yellowish red |
| 142 | H | —CH$_3$ | " | | yellow |

TABLE-continued

| Example | Diazo component Y | X | R | Coupling component | |
|---|---|---|---|---|---|
| 143 | H | —CH₃ | " | 2-methylindole structure | reddish yellow |
| 144 | H | —CH₃ | 4-SO₃H, 2-CONH, 5-Cl phenyl | " | reddish yellow |
| 145 | H | —CH₃ | " | N,N-diethyl-3-methylaniline | yellowish red |
| 146 | H | —CH₃ | " | pyrazolone with phenyl | yellow |
| 147 | H | —H | " | " | yellow |
| 148 | H | —Cl | " | " | yellow |
| 149 | H | —Cl | " | N,N-diethyl-3-methylaniline | yellowish red |
| 150 | H | —H | " | " | yellowish red |

TABLE-continued
| Example | Diazo component | | | Coupling component | |
|---|---|---|---|---|---|
| | Y | X | R | | |
| 151 | H | —CH₃ | 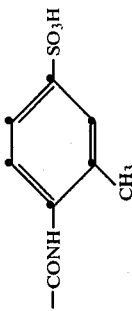 | " | yellowish red |
| 152 | H | —CH₃ | 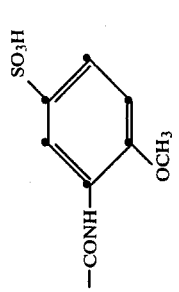 | " | yellowish red |
| 153 | H | —CH₃ | 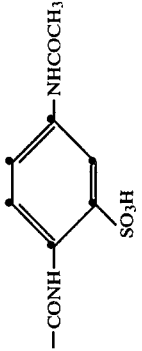 | " | yellowish red |
| 154 | H | —CH₃ | 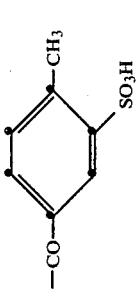 | | yellowish red |
| 155 | H | —CH₃ | " | | reddish yellow |
| 156 | H | —CH₃ | " | | yellow |

TABLE-continued

| Example | Diazo component | | | Coupling component | Shade on wool |
|---|---|---|---|---|---|
| | Y | X | R | | |
| 157 | H | —H | " | 3-methyl-N,N-diethylaniline | yellowish red |
| 158 | H | —Cl | " | " | yellowish red |
| 159 | H | —H | " | 2-methylindole | reddish yellow |
| 160 | H | —Cl | " | " | reddish yellow |
| 161 | H | —H | " | 1-phenyl-3-methyl-5-aminopyrazole | yellow |
| 162 | H | —Cl | " | 3-methyl-N,N-diethylaniline | yellow |
| 163 | H | —CH₃ | 2-chloro-5-sulfobenzoyl | " | yellowish red |
| 164 | H | —H | " | " | yellowish red |
| 165 | H | —Cl | " | " | yellowish red |

TABLE-continued

| Example | Diazo component | | | Coupling component | |
|---|---|---|---|---|---|
| | Y | X | R | | |
| 166 | H | —CH₃ | —SO₂NH— ⌬—SO₃H | [naphthalene with OH, NHCO-phenyl-NHCOCHBr-CH₂Br, 2×SO₃H] | red |
| 167 | H | —Cl | " | " | red |
| 168 | H | —CH₃ | —CONH— ⌬—SO₃H | " | red |
| 169 | H | —CH₃ | —SO₂NHCH₂CH₂SO₃H | " | " |
| 170 | H | —CH₃ | —CO— ⌬(CH₃)(SO₃H) | " | red |
| 171 | H | —CH₃ | —SO₂NH— ⌬—SO₃H | [naphthalene with OH, NHCO-phenyl-NHCOCHBr-CH₂Br, SO₃H, SO₃H] | red |

| | Diazo component | | | Coupling component | |
|---|---|---|---|---|---|
| Example | Y | X | R | | |
| 172 | H | —CH$_3$ | " | 2-hydroxy-3-(NHCOCHBrCH$_2$Br)-6-SO$_3$H naphthalene | yellowish red |
| 173 | H | —CH$_3$ | " | 2-hydroxy-3-[N(CH$_3$)COCHBrCH$_2$Br]-6-SO$_3$H naphthalene | reddish orange |
| 174 | H | —CH$_3$ | " | 2-hydroxy-3-{NHCO-[3-(NH-(4,6-difluoro-5-chloropyrimidin-2-yl))phenyl]}-6-SO$_3$H naphthalene | red |
| 175 | H | CH$_3$ | 3-SO$_3$H-phenyl-SO$_2$NH— | N-ethyl-N-benzyl aniline | red |
| 176 | H | H | " | " | red |
| 177 | H | Cl | " | " | red |

TABLE-continued

| Example | Diazo component Y | X | R | Coupling component | |
|---|---|---|---|---|---|
| 178 | H | CH$_3$ | 3-SO$_2$NH-, 4-SO$_3$H-phenyl | " | red |
| 179 | H | H | " | " | red |
| 180 | H | Cl | " | " | red |
| 181 | H | CH$_3$ | 4-SO$_2$NH-, 3-SO$_3$H-phenyl | " | red |
| 182 | H | H | " | " | red |
| 183 | H | Cl | " | " | red |
| 184 | H | Cl | 4-CONH-, 3-SO$_3$H-phenyl | " | red |
| 185 | H | Cl | —SO$_2$NHCH$_2$CH$_2$SO$_3$H | " | red |
| 186 | H | Cl | 4-SO$_2$NH-, 3-SO$_3$H-phenyl | " | red |
| 187 | H | H | " | 4-N(C$_4$H$_9$)$_2$, 2-CH$_3$-phenyl | red |
| 188 | H | CH$_3$ | 3-SO$_2$NH-, 4-SO$_3$H-phenyl | " | red |
| 189 | H | H | " | " | red |
| 190 | H | Cl | " | " | red |
| 191 | H | Cl | —SO$_2$NHCH$_2$CH$_2$SO$_3$H | " | red |

TABLE-continued

| Example | Diazo component Y | Diazo component X | Diazo component R | Coupling component | |
|---|---|---|---|---|---|
| 192 | H | Cl | ![-SO2NH-phenyl with SO3H] | N(C2H5)(CH2CH2OH) on phenyl with CH3 | red |
| 193 | H | CH3 | " | " | red |
| 194 | H | H | " | " | red |
| 195 | H | Cl | -SO2NH-phenyl with SO3H (para) | " | red |
| 196 | H | Cl | " | N(C2H5)(C3H7) on phenyl with CH3 | red |
| 197 | H | CH3 | " | " | red |
| 198 | H | H | " | " | red |
| 199 | H | CH3 | -SO2NHCH2CH2SO3H | " | red |
| 200 | H | H | -SO2NH-phenyl with SO3H | naphthyl-N(H)(CH3) with ethyl | red |
| 201 | H | Cl | " | " | red |
| 202 | H | H | " | " | red |
| 203 | H | CH3 | " | " | red |

TABLE-continued

| Example | Diazo component | | | Coupling component | |
|---|---|---|---|---|---|
| | Y | X | R | | |
| 204 | Cl | Cl | 3-SO₂NH-4-SO₃H-phenyl | 4-N(C₂H₅)₂-3-CH₃-phenyl | red |
| 205 | Cl | Cl | 4-SO₂NH-3-SO₃H-phenyl | " | red |
| 206 | Cl | Cl | 4-SO₂NH-3-SO₃H-phenyl | " | red |
| 207 | Cl | Cl | 3-SO₂NH-4-SO₃H-phenyl | 4-N(CH₃)(CH₂CH₂OH)-3-CH₃-phenyl | red |
| 208 | Cl | Cl | 4-SO₂NH-3-SO₃H-phenyl | " | red |
| 209 | Cl | Cl | 4-SO₂NH-3-SO₃H-phenyl | " | red |
| 210 | Cl | Cl | 3-SO₂NH-4-SO₃H-phenyl | " | red |

TABLE-continued
| Example | Diazo component | | | Coupling component | |
|---|---|---|---|---|---|
| | X | Y | R | | |
| 211 | Cl | Cl | 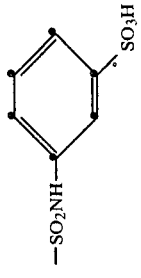 —SO₂NH—C₆H₃(SO₃H) | " | red |
| 212 | Cl | Cl | —SO₂NH—C₆H₃(SO₃H) | " | red |
| 213 | Cl | Cl | —SO₂NH—C₆H₃(SO₃H) | 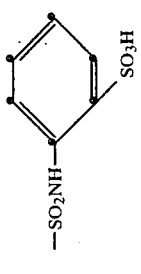 C₆H₄—N(CH₂CH₂OH)₂ | red |
| 214 | Cl | Cl | —SO₂NH—C₆H₃(SO₃H) | " | red |
| 215 | Cl | Cl | —SO₂NH—C₆H₄(SO₃H) | " | red |
| 216 | Cl | Cl | —SO₂NH—C₆H₃(SO₃H) | 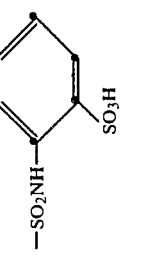 C₆H₃(CH₃)—N(CH₂CH₂OH)₂ | red |

TABLE-continued

| Example | Diazo component | | | Coupling component | |
|---|---|---|---|---|---|
| | Y | X | R | | |
| 217 | Cl | Cl | 4-(SO₂NH-)benzene-SO₃H | 4-methyl-2-N(CH₂CH₂OH)₂-phenyl | red |
| 218 | Cl | Cl | 4-(SO₂NH-)benzene-SO₃H | " | red |
| 219 | Cl | Cl | 3,4-(SO₂NH-,SO₃H)benzene | 3-methyl-N(C₂H₅)(CH₂-C₆H₄-SO₃H)-aniline | red |
| 220 | Cl | Cl | 3-(SO₂NH-)benzene-SO₃H | " | red |
| 221 | Cl | Cl | 4-(SO₂NH-)benzene-SO₃H | " | red |

*In these cases (Examples 55 and 56), the coupling components used in the coupling were not those indicated in the table but the corresponding free hydroxy compounds, i.e. phenol and naphthol respectively, and the hydroxyl groups were akylated after the coupling. The reason the table shows for Examples 55 and 56 the already etherified hydroxy compounds as coupling components is merely to clarify the structure of the end products.

Dyeing method I 10 parts of Helanca jersey are dyed in 500 parts of an aqueous liquor which contains per liter 1 g of monosodium phosphate and which has been brought to pH 6 by means of disodium phosphate. The amount of the dye of Example 6 is 1.4% on weight of fibre. The dyeing time at a temperature of 98% is 30-90 minutes. The dyed Helanca fabric is then taken out of the bath and conventionally washed and dried.

This gives a deep red Helanca fabric which has a bright shade and very good overall fastness properties and which is in particular very resistant to formuladehyde.

Dyeing method II 10 parts of wool fabric are dyed in 500 parts of an aqueous liquor which contains, on weight of fibre, 4% by weight of ammonium sulfate, 1.5% by weight of 80% acetic acid, 1% by weight of a substituted alkylaminopolyglycol ether and 3% by weight of the dye of Example 10, at a temperature of 98° for 30 to 90 minutes. The bath is then cooled down to 80° and is neutralised by adding 2.5% by weight of 25% aqueous ammonia, and the dyeing is completed at this temperature in the course of 15 minutes. The dyed wool fabric is then taken out of the bath and conventionally washed and dried.

This gives a wool fabric which has a bright shade and good overall fastness properties.

What is claimed is:

1. A monoazo dye of the formula

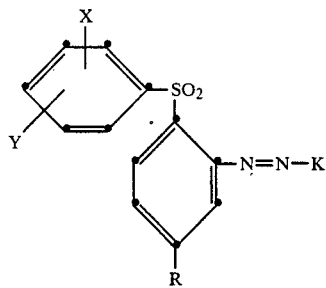

in which K is an aminobenzene, alkoxybenzene, aminonaphthalene, alkoxynaphthalene, naphthol, aminonaphthol, pyrazolone, aminopyrazole, pyridone pyrimidine, indole, naphthimidazole, diphenylamine, pyrazolo[2,3-a]pyrimidine, tetrahydroquinoline or acetoacetamide radical, and R is

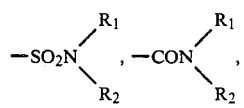

$-CO-R_2$ or $-SO_2-O-R_2$ in which $R_1$ is hydrogen or $C_{1-4}$-alkyl and $R_2$ is monosulfo-$C_{1-12}$-alkyl which is unsubstituted or substituted by halogen, hydroxyl, cyano, $C_{1-4}$-alkoxy, $C_{1-6}$-alkanoyl or benzoyl, or a radical of the formulae

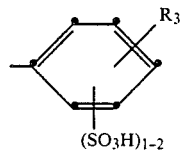

or

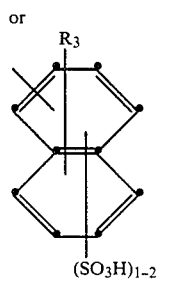

where $R_3$ in the formulae (2) and (3) is hydrogen, $C_{1-4}$-alkyl, $C_{1-4}$-alkoxy, halogen, $C_{2-6}$-alkanoylamino or carboxyl, and X and Y, independently of each other, are hydrogen, $C_{1-4}$-alkyl, $C_{1-4}$-alkoxy, halogen, $C_{2-6}$-alkanoylamino, $C_{1-5}$-alkylsulfonylamino, phenyl which is unsubstituted or substituted by $C_{1-4}$-alkyl, $C_{1-4}$-alkoxy, halogen, $C_{1-6}$-alkanoyl amino, hydroxyl or carboxyl, or phenoxy which is unsubstituted or substituted by $C_{1-4}$-alkyl, $C_{1-4}$-alkoxy, halogen, $C_{1-6}$-alkanoylamino, hydroxyl or carboxyl.

2. A monoazo dye according to claim 1, in which $R_2$ is an unsubstituted monosulfo-$C_{1-12}$-alkyl radical, a radical of the formula

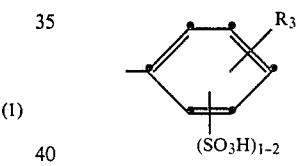

or a radical of the formula

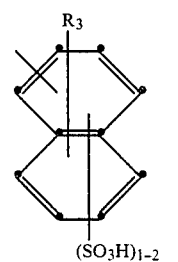

where and K, R, $R_1$, $R_3$ X Y are as defined in claim 1.

3. A monoazo dye according to claim 2, in which Y is hydrogen, chlorine or methoxy, and K, R, $R_1$, $R_2$, $R_3$ and X are as defined in claim 2.

4. A monoazo dye according to claim 3, in which X is bonded to the phenyl ring in p-position relative to the $-SO_2$ group, and K, R, $R_1$, $R_2$, $R_3$ and Y are as defined in claim 3.

5. A monoazo dye according to claim 4, in which K is N-$C_{1-4}$-alkylaminobenzene or N,N-di-$C_{1-4}$-alkylaminobenzene which is unsubstituted or substituted in the benzene ring by methyl, chlorine, acetylamino and benzoylamino and in which the N-alkyl is unsubstituted or substituted independently of each other by hydroxyl, chlorine, cyano, phenyl or sulfophenyl, methoxybenzene, methoxynaphthalene, aminonaphthalene which is unsubstituted or substituted by sulfo, or K is hydroxynaphthalene which is unsubstituted or substituted by sulfo, or K is aminonaphthol which is unsubstituted or substituted in the naphthalene nucleus by sulfo and in which the amino group is unsubstituted or substituted by methyl, α,β-dibromopropionyl, α,β-dibromopropionylaminobenzoyl and 2,6-difluoro-5-chloro-pyrimidylaminobenzoyl, 1-phenyl-3-methylpyrazolone which is unsubstituted or substituted in the phenyl by chlorine and methyl, 1-phenyl-3-methylaminopyrazole which is unsubstituted or substituted in the phenyl by chlorine and sulfo, 1-ethyl-4-methyl-6-hydroxypyrid-2-one which is unsubstituted or substituted in the 3-position by carbamoyl, 2,4,6-triaminopyrimidine, 2-methylindole or 1-ethyl-2-methylindole, 1-chlorophenylamino-2-methylnaphthimidazole or 2-pentylnaphthimidazole which is unsubstituted or substituted in the naphthalene nucleus by hydroxyl and sulfo, N-methyl or N-ethyl-1,2,3,4-tetrahydroquinoline, or 2,5-dimethyl-7-aminopyrazolo[2,3-a]pyrimidine, and R is

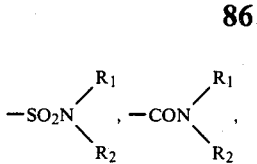

—CO—R$_2$ or —SO$_2$—O—R$_2$ in which R$_1$ is hydrogen or methyl, and R$_2$ is β-sulfoethyl, 2-, 3- or 4-sulfophenyl in which the phenyl ring is unsubstituted or substituted by methyl, methoxy, chlorine, acetylamino and carboxyl, 2,5-disulfophenyl, monosulfonaphthyl or disulfonaphthyl, X is hydrogen, methyl, chlorine, ethoxy, acetylamino or phenoxy, and Y is hydrogen, chlorine or methoxy.

6. A monoazo dye according to claim 5, in which K is N,N-di-C$_{1-4}$-alkylaminobenzene which is unsubstituted or substituted in the benzene nucleus by methyl, chlorine, acetylamino and benzoylamino and in which the N-alkyl is unsubstituted or substituted independently of each other by hydroxyl, chlorine, cyano, phenyl or sulfophenyl, 1-phenyl-3-methylaminopyrazole which is unsubstituted or substituted in the phenyl by chlorine and sulfo, or 2-methylindole or 1-ethyl-2-methylindole, and R, X and Y are as defined in claim 5.

7. A monoazo dye according to claim 6, in which K is an N,N-diethyl-3-methylaniline, N-ethyl-N-β-hydroxyethyl-3-methylaniline, 1-phenyl-3-methyl-5-aminopyrazole or 2-methylindole, R is β-sulfoethylaminosulfonyl, o-sulfophenylaminosulfonyl, p-sulfophenylaminosulfonyl, p-sulfophenylaminocarbonyl or p-methyl-m-sulfobenzoyl, X is methyl or chlorine, and Y is hydrogen.

* * * * *